United States Patent
Wolfe et al.

(10) Patent No.: US 8,558,194 B2
(45) Date of Patent: Oct. 15, 2013

(54) INTERACTIVE COATINGS, SURFACES AND MATERIALS

(75) Inventors: Douglas E. Wolfe, St. Marys, PA (US);
Matthew Kelly, State College, PA (US);
Brian M. Gabriel, Joppa, MD (US)

(73) Assignee: The Penn State Research Foundation, University Park, PA (US)

( * ) Notice: Subject to any disclaimer, the term of this patent is extended or adjusted under 35 U.S.C. 154(b) by 384 days.

(21) Appl. No.: 12/798,706

(22) Filed: Apr. 9, 2010

(65) Prior Publication Data

US 2010/0260926 A1    Oct. 14, 2010

Related U.S. Application Data

(60) Provisional application No. 61/168,469, filed on Apr. 10, 2009.

(51) Int. Cl.
*G01N 21/64* (2006.01)
*G21G 5/00* (2006.01)
*C09K 11/02* (2006.01)

(52) U.S. Cl.
USPC ............. 250/461.1; 250/492.1; 252/301.4 R

(58) Field of Classification Search
USPC ......... 250/461.1, 492.1, 432 R, 458.1, 559.4,
250/302; 252/301.4 R; 427/8; 428/411.1
See application file for complete search history.

(56) References Cited

U.S. PATENT DOCUMENTS

| | | | | |
|---|---|---|---|---|
| 2,320,842 A | 6/1943 | Arnold et al. | | |
| 2,976,716 A | 3/1961 | De Haven | | |
| 3,995,157 A | 11/1976 | Holub et al. | | |
| 4,250,382 A * | 2/1981 | Libby | ............ | 250/302 |
| 4,327,155 A | 4/1982 | Hanneman | | |
| 5,625,456 A * | 4/1997 | Lawandy | ............ | 356/601 |
| 6,974,641 B1 | 12/2005 | Choy et al. | | |
| 2008/0305244 A1 | 12/2008 | Cui et al. | | |

FOREIGN PATENT DOCUMENTS

| WO | WO 95/32060 A1 | 11/1995 |
|---|---|---|
| WO | WO 02/28973 A1 | 4/2002 |
| WO | WO 02/071045 A2 | 9/2002 |

OTHER PUBLICATIONS

Hirai, Takayuki et al., "Preparation of Y2O3:Yb,Er Infrared-to-Visible Conversion Phosphor Fine Particles Using an Emulsion Liquid Membrane System", Chem. Mater. 2002, 14, pp. 3576-3583.
Molecular Expressions(TM), "Optical Microscopy Primer, Specialized Techniques, Fluorescence Microscopy, Basic Concepts in Fluorescence", http://micro.magnet.fsu.edu/primer/techniques/fluorescence/fluorescenceintro.html (1 of 21) printed Jul. 8, 2010.
The Penn State Research Foundation, PCT/US2010/030549, International Search Report and the Written Opinion of the International Searching Authority, Jun. 17, 2010, 14 Pages.

* cited by examiner

*Primary Examiner* — David Porta
*Assistant Examiner* — Faye Boosalis
(74) *Attorney, Agent, or Firm* — McKee, Voorhees & Sease, P.L.C.

(57) ABSTRACT

The present invention provides in-situ health monitoring and non-destructive evaluation and early detection of corrosion, damage, failure, flaws, defects, and subsurface inspection by the generation of electromagnetic responsive surfaces, coatings and coating systems.

26 Claims, 8 Drawing Sheets
(8 of 8 Drawing Sheet(s) Filed in Color)

INTERACTIVE COATINGS, SURFACES AND MATERIALS

CROSS-REFERENCE TO RELATED APPLICATIONS

This application claims priority under 35 U.S.C. §120 of a provisional application Ser. No. 61/168,469 filed Apr. 10, 2009, which application is hereby incorporated by reference in its entirety.

FIELD OF THE INVENTION

The present invention relates generally to a technique for post, in-situ health monitoring and/or nondestructive evaluation and early detection of corrosion, damage, failure, flaw/defect detection, subsurface inspection, and the like by providing electromagnetic responsive/interactive materials, coatings and coating systems.

BACKGROUND OF THE INVENTION

The statements in this section merely provide background information related to the present invention and may not constitute prior art.

Corrosion is the leading cause of material failure costing billions annually in the United States. The largest sector of corrosion prevention is that of protective, organic and metallic coatings applied to ferric components. Small defects and damage of the protective coating acts as initiation sites for subsurface component degradation. Further enunciation of the effects of corrosion is evident by damage caused from erosion, impact, wear, chemical changes, or a combination of the like. Preventive maintenance applied to damaged or locally corroded areas prevents further corrosion and avoids the costs of component or overall structural replacement. The extent of damage to a painted or coated material can be difficult to evaluate due to a number of factors, not limited to, small flaw size, low contrast between feature and nominal coating, inspection resolution, coloring or staining of surface to be inspected, operator error, and the like. In many circumstances, surface damage and degradation are not the only concerns that exist. For example, subsurface coatings assist with galvanic protection by providing additional resistance to corrosion, nuclear radiation and electromagnetic radiation. That said, failure of a subsurface coating, like surface coatings, can result in failure of a component or entire structure/product. Additionally, small subsurface cracks not readily visible using surface inspection techniques can lead to degradation, fatigue, and ultimately structural failure. Therefore, there is a need in the art to provide a coating that can be used to provide a method for inspecting the integrity of surface and subsurface coatings. Visual inspection is one primary method of damage detection. However, visual inspection has a low probability of detecting small flaws and is time consuming. Therefore, there is a need in the art to provide a coating having increased inspection rates due to increased contrast of flawed areas, and thus resulting in a higher level of detection of flaws overall.

Other techniques also exist for nondestructive evaluation or inspection. For example, Liquid Dye Penetrant (LDP) testing is one primary nondestructive evaluation process. This process may include cleaning the surface to be inspected, applying liquid penetrant dye, removing excess penetrant, applying developing solution, and inspecting surface for flaws. The dye for penetrant inspection is typically of a contrasting color, fluorescent material, or a UV interactive material to enhance detection by visual inspection.

Although used as a primary nondestructive evaluation inspection technique, LPD has its limitations. For example, LPD requires costly consumables for detection. The coating/coating system or component has to be exposed to the coating surface in order to be detected and may be difficult to evaluate the surface for flaws as a result of the small flaw size, low contrast between feature and nominal coatings, inspection resolution, coloring or staining of the surface to be inspected, and/or operator error, and the like. Similarly, LPD inspection is limited to a minimum depth and is not practical for large area detection.

Magnetic Particle Inspection (MPI) is an alternative nondestructive evaluation inspection technique for ferric structures. MPI may include applying to the surfaces of inspection UV reactive material, applying a magnetic field to the component of inspection and inspecting the part under UV illumination. MPI is typically only conducted on small components due to the requirement of magnetization of the component to be inspected. Similarly, like LPD, MPI requires additional consumables, is time consuming, and is limited to relatively small magnetically compatible components.

Coatings have been shown to be an effective way of monitoring, determining and detecting corrosion, damage, flaws/defects, and the like, and as such, have been the subject of several patents. For example, U.S. Pat. No. 2,320,842 to Arnold et al discloses the use of luminescent pigment for primers and automotive paint to determine thin top coatings. U.S. Pat. No. 4,327,155 to Hanneman discloses using a luminescent layer of flame spray coatings for detection of penetration depth of erosion for ceramic and metallic components. U.S. Pat. No. 2,976,716 to Haven teaches a method of determining wear patterns using multi-layer paint with color variations. Lastly, U.S. Pat. No. 6,974,641 to Choy et al discloses a thermal barrier coating with a thermal luminescent indicator material embedded therein. Although the above-mentioned references disclose various coatings used to detect wear, erosion, and other desirable evaluation indicators, the above references do not disclose a technique for producing "smart" coatings or coating systems for health monitoring and/or nondestructive evaluation and early detection that when stimulated, apprise of failure zones that include corrosion sites, damage regions, flaws, defects within a protective layer, and the like.

The present invention addresses needs in the art for improved coating and coating systems for in-situ health monitoring, subsurface inspection, nondestructive evaluation and/or early detection of corrosion, damage, failure, flaws, defects, and the like.

BRIEF SUMMARY OF THE INVENTION

Further areas of applicability of the present invention will become apparent from the description provided herein. It should be understood that the description includes specific examples that are intended for purposes of illustration and are not intended to limit the scope of the present teachings.

In one aspect of the present invention, a material, coating or coating system for non-destructively detecting and evaluating surface and subsurface regions of a surface or coated structure using one or more stimulates is disclosed. The coating system includes a layer or region with one or more interactive materials adapted to provide an emission response when stimulated.

In yet another aspect of the present invention, a method for non-destructively detecting and evaluating surface and subsurface regions of a material, coating or coated structure using one or more electromagnetic stimulates is disclosed. The method includes stimulating the interactive materials with the electromagnetic stimulate and detecting an emission response from the material, coating or coated structure to evaluate the health of the surface and/or subsurface regions.

BRIEF DESCRIPTION OF THE DRAWINGS

The file of this patent contains at least one drawing executed in color. Copies of this patent with colored drawing(s) will be provided by the Patent and Trademark Office upon request and payment of the necessary fee.

The drawings described herein are for illustration purposes only and are not intended to limit the scope of the present disclosure in any way.

DETAILED DESCRIPTION OF THE PREFERRED EMBODIMENT

The following description is merely exemplary in nature and is not intended to limit the present disclosure, application, or uses.

The present invention generally provides for a technique for in-situ health monitoring and/or nondestructive evaluation and early detection of corrosion, damage, failure, flaws, defects, subsurface inspection, and the like by providing electromagnetic responsive surfaces, coatings and coating systems. A further aspect of the present invention provides a technique for producing built-in "smart" coatings, materials, layers, components, regions or coating systems for health monitoring and/or nondestructive evaluation and early detection so that when stimulated, the surface(s), coating(s) or coating systems emit electromagnetic waves at or near failure zones that include, but are not limited to, corrosion sites, damaged areas, flaws, defects within a protective layer, and the like. A still further aspect of the present invention includes, but is not limited to, the following applications: (1) protective coating inspection; (2) intra-layer interfaces of multi-layer coating systems; (3) subsurface inspection of protective coatings and substrates. The present invention should not be construed as being limited in application. The electromagnetic illumination, stimulation-interaction-emission of electromagnetic waves of the present invention may be used in many high-volume commercial applications. These applications may include, but are not limited to, integrity inspection of subsurface regions, layers and material surfaces for adhesion and blistering detection, paint systems for automotive applications, bridges, buildings, structures, military components, ships, and space vehicles.

In another aspect of the present invention, the electromagnetic illumination, stimulation-interaction-emission of electromagnetic waves may be broadly classified into the following interactive electromagnetic categories based on the electromagnetic stimulation and emission response: UV (ultra-violet, 10-400 nm wavelength), visible (380-760 nm wavelength), and IR (Near IR 750-2500 nm, Mid IR 2500-1000 nm, & Far IR 10000 nm-1 mm). Electromagnetic waves in the visible range can be detected by visual inspection, while UV and IR waves can be detected with appropriate imaging device to provide detection or enhanced detection.

Figure 1:
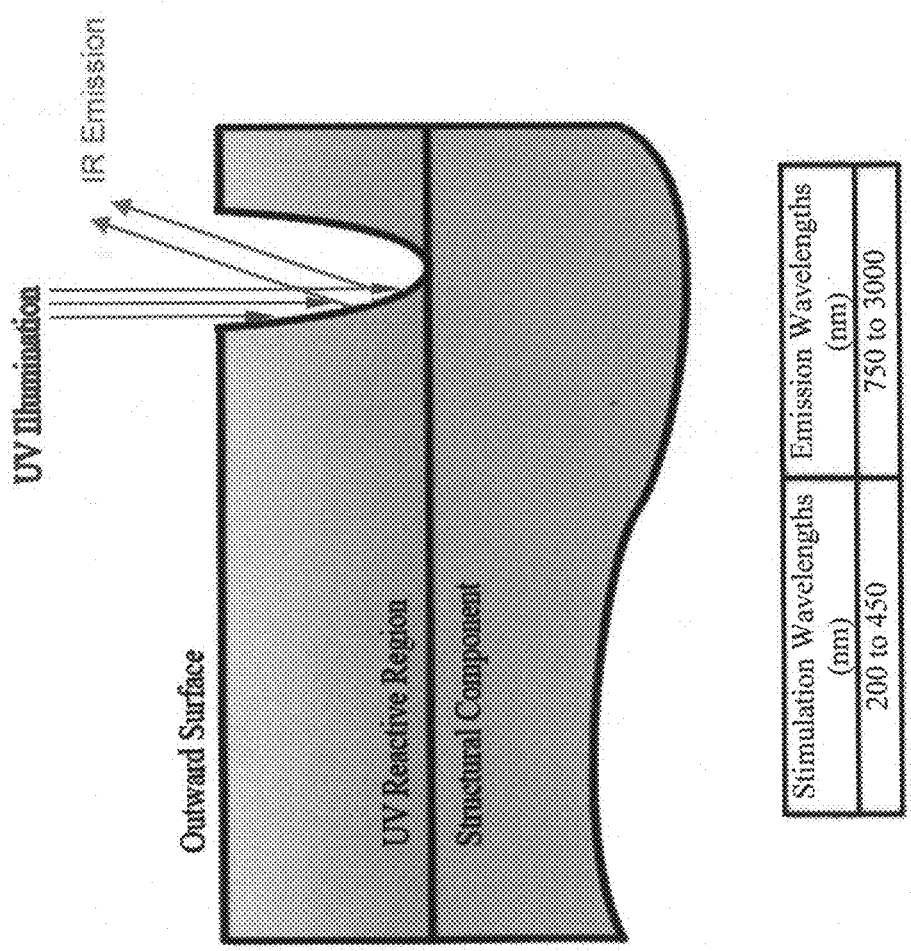
FIG. 1 is a schematic of a protective coating UV, visible, or IR reactive sensing region to produce a smart coating for damage detection wherein the coating system shown is for a UV responsive coating according to an exemplary embodiment of the present invention.
Figure 2:
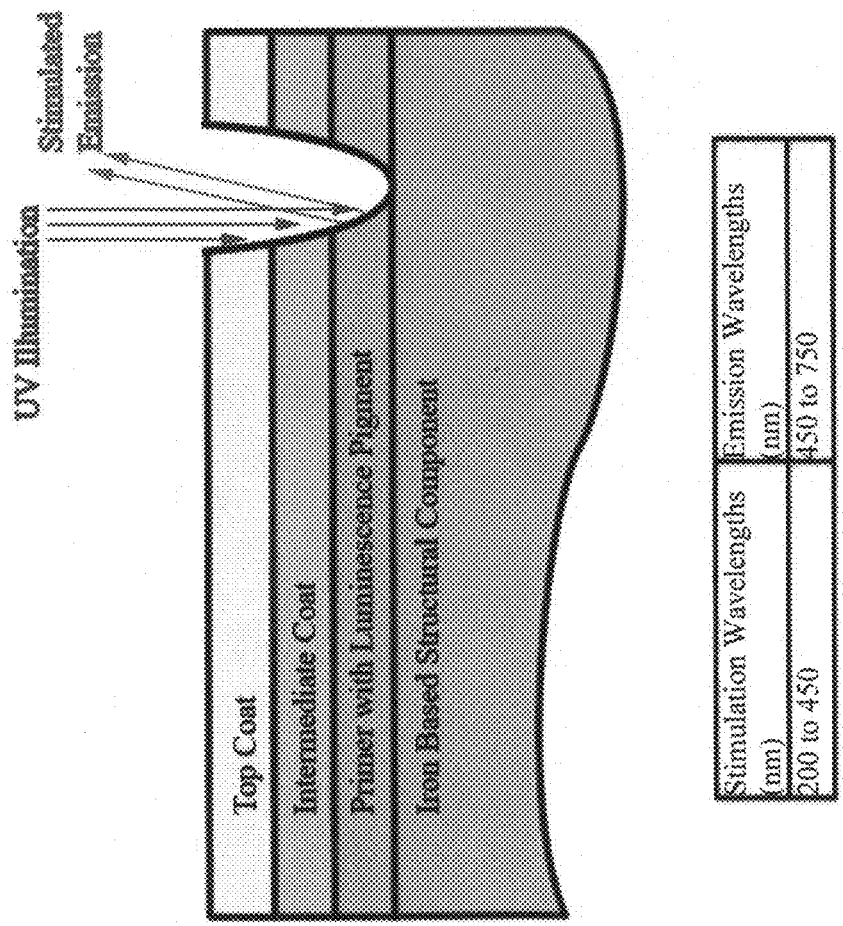
FIG. 2 is a schematic of a multiple layer protective coating with a UV reactive sensing primer for damage detection according to an exemplary embodiment of the present invention.
Figure 6:
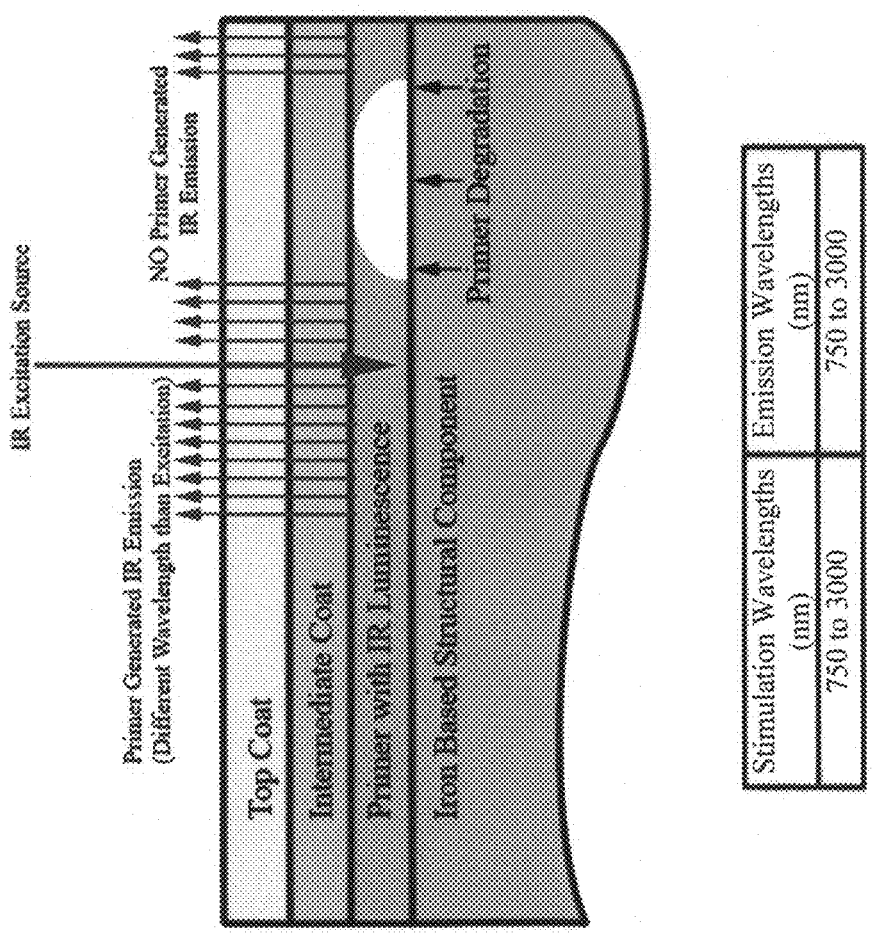
FIG. 6 is a schematic illustrating how damage to a primer layer can be detected as a dark region (or opposite contrast) in the emission response.
Figure 7:
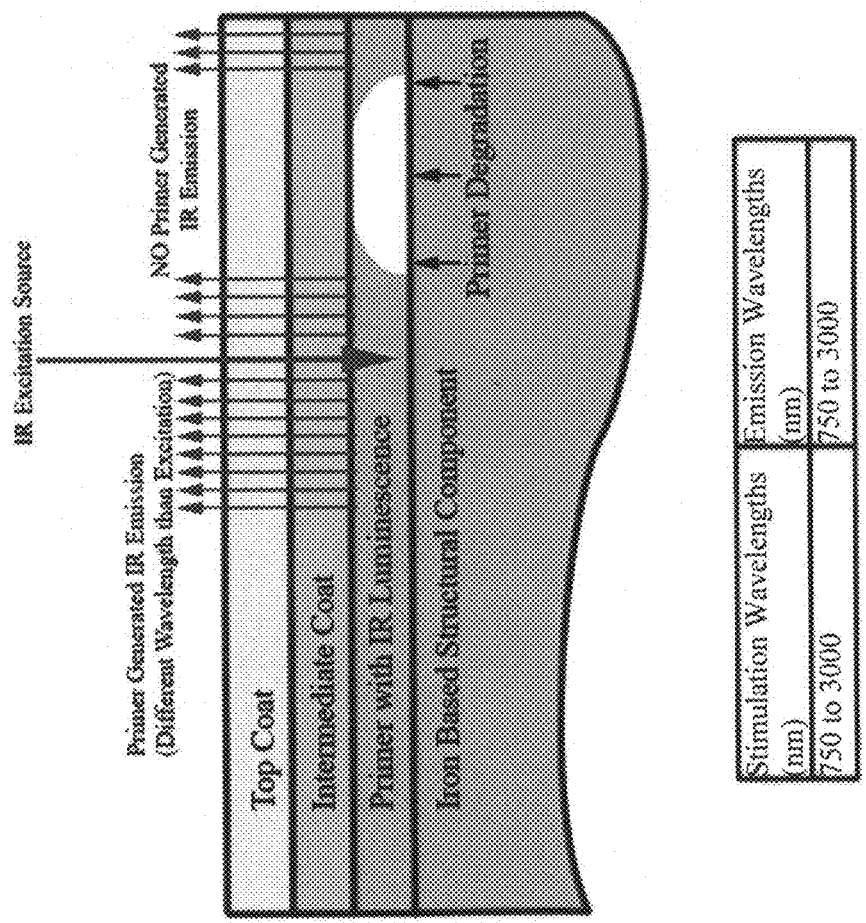
FIG. 7 is a schematic illustrating how damage to a primer layer can be detected as a dark region (or opposite contrast) in the emission response using IR detecting photography or video equipment according to another aspect of the present invention.
Figure 8:
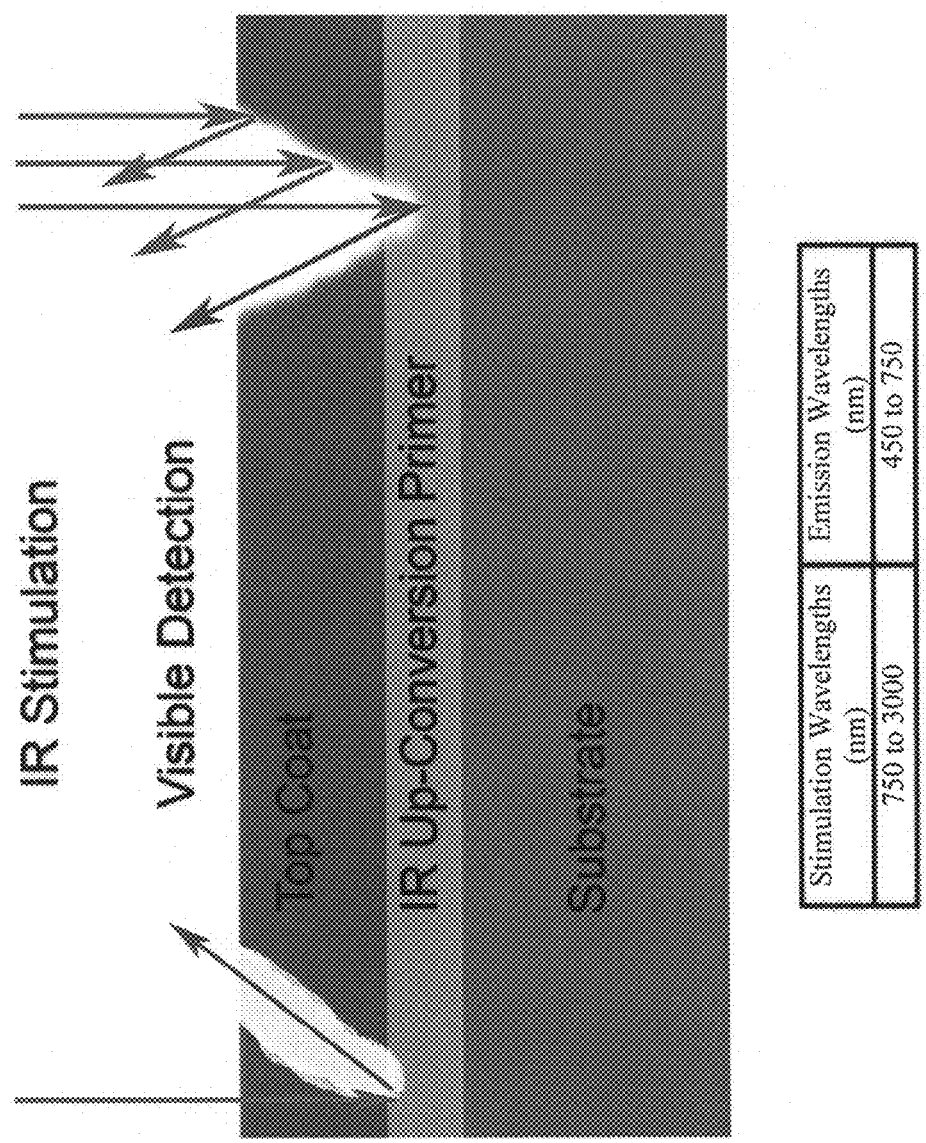
FIG. 8 is a schematic illustrating how damage to subsurface features or the depth of a primer can be detected using IR stimulated up-conversion pigments having visual luminescence in accordance with an exemplary embodiment of the present invention.

In a further aspect of the present invention, electromagnetic emission classes (subclassifications) may include:
1. UV stimulation to IR Emission. As shown in FIG. 1, Interactive surfaces, coating and coating systems for enhanced non-destructive evaluation and detection of corrosion, failure, damage, blistering, adhesion, flaws, and or defects;
2. UV Stimulation to Visual Emission: As shown in FIG. 2, UV interactive coating and coating systems for nondestructive evaluation and detection of corrosion, failure, damage, flaw, and/or defects;
3. IR Up-Conversion to IR Emission: As shown in FIG. 6, IR interactive coatings and coating systems for nondestructive evaluation (NDE), surface inspection (IR stimulated long-visual emission), and subsurface inspection which provide increased safety over UV detection, greater inspection distances, corrosion damage, adhesion/blistering and increased luminescence through penetration of stimulated frequencies;
4. IR Down-Conversion to IR Emission: As shown in FIG. 7, IR interactive coatings and coating systems for subsurface NDE inspection between 750-3000 nm (IR stimulated long-IR emission) and ≈750-3000/upwards of 3000 nm for subsurface structural inspection;
5. IR Up-Conversion to Visible Emission: As shown in FIG. 8, IR interactive coatings and coating systems for subsurface NDE inspection between 750-3000 nm (IR stimulated long-emission) and ≈750-3000 nm for surface and subsurface coating inspection;
6. Any combination of 1-5, above.

In a preferred form, the present invention provides a technique to produce coatings or coating systems that emit electromagnetic waves when exposed to electromagnetic stimulation of wavelengths between 1-3000 nm. Thus, the present invention overcomes the limitations in the art by providing wavelengths of stimulation and emission of interactive/reactive surfaces, coatings, and coating systems as well as position of depth within a coating or coating system. The present invention contemplates that the system may be built-in to a coating, coating system, layer, material, component, region, surface (coated or uncoated), or the like.

Electromagnetic emission is generated typically through up-conversion or down-conversion stimulation. Down-conversion is generation of a lower energy wave from a higher energy wave. Up-conversion is the generation of a high energy wave from multiple lower energy waves. The phosphors may be present in the coating system as a second phase, such as a pigment, or the luminescent center, which may be inseparable from the coating system, such as a molecular side or end group attached to one of the primary or secondary components of the coating system. Thus, a solution to flaw, corrosion, damage detection, blistering, and the like is provided by the present invention in the interaction and responsive interactive coatings between the "smart coating", protective coatings and/or the substrate. Although damage, whether visible or exposed, is typically a result of corrosion, cracks, abrasions, wear sites, blistering, erosion sites, and the like, the present invention allows detection of damage and/or damage sites, even though not visible or exposed to the outer surface for detection. For example, electromagnetic frequencies in the IR range (750-3000 nm) can transmit through most organic coating systems causing stimulation (e.g., damage sites or flaws which luminescence electromagnetic radiation provides a high contrast to the non-damaged or non-flawed surface, coating and coating systems). High contrast of the damage and flaw sites in electromagnetic response coatings and coating systems provides a significant improvement to the nondestructive evaluation/detection of flaws over traditional coatings and coating systems. Stimulated electromagnetic emission for the present invention may be categorized into three primary categories: UV (ultra-violet, 10-400 nm wavelength), visible (400-750 nm wavelength) and IR (Infrared greater than 750 nm wavelength, but less than 1 mm). The wavelength ranges provided are merely for the purposes of providing example applications of the present invention and should not be construed as limiting the scope of the present invention. Electromagnetic waves in the visible range can be detected by a visual inspection, while UV and IR waves can be detected with appropriate imaging devices. Electromagnetic waves in the IR range can also penetrate outward surface coatings and generate emission in subsurface layers. Subsurface IR generated emission will penetrate outward coatings and can be detected and used to assess subsurface integrity.

Other applications of the present invention include conversion of light with lower energy than UV to UV producing, localized UV curing or degradation of polymer components to alter stress states, density, and hardness to produce components with an engineered structure. Higher up-conversion to UV luminescent coating systems preferably use a stimulation wavelength (750-3000 nm) and emission wavelengths 10-450 nm).

Examples of luminescent materials exist in a wide array of compounds, such as natural oxides, doped ceramic crystals, polymers, and some plants and animals. Stimulation of these compounds can be facilitated from many sources ranging from thermal excitation and electromagnetic waves to chemical reactions and high energy particle impacts. Some examples of luminescent materials include naturally occurring luminescent minerals, cadinion solenoid Quantum Dots of different particle size and bio-luminescent jelly fish.

The basic principles of luminescence are described by electrons in shells around atoms at or near room temperature which typically occupy the lowest unfilled electron shell or the "ground state". The energy absorbed by the electrons causes excitation to higher states. The amount of energy absorbed by electrons due to electro-magnetic stimulation, and wavelength of emission from electrons returning to the ground state can be calculated using Planck's law. It is important to note that electrons cannot reside between bands and internal band transitions are dissipated into the material as lattice vibrations (heat).

Emission for a luminescent material can be a very narrow peak, a wide spectrum in nearly any wavelength range, or multiple peaks corresponding to the different available level transitions. Thus, luminescent material selection, with its many choices, should accommodate other layers and meet other requirements such as high levels of emission, long lasting luminous properties, and low production and processing costs.

Initial materials were selected to span a range of luminescence and powder properties to identify the requirements of a pigment for primer incorporation. The key properties of interest included, for example, luminescence efficiency due to UV excitation, particle size (small particle size powders provide more luminescent centers per unit area for the same solids loading as larger particle size powders), powder density (low density powders have more luminescent centers for the same solid loading as high density powders), powder morphology, surfactants, and the dispersants. By way of an example, additional ceramic powders were selected and processed to provide better emission and incorporation into zinc base primers. As indicated above, small particle size powders provide more luminescent centers per unit area for the same solid loading as larger particle size powders. For example fine powders are those with an average particle size <5 microns, mid size are those with an average particle size in the 5 micron to 15 micron range, and coarse size powders are those with an average particle size greater than approximately 15 microns, which are typically not used as pigments. To demonstrate the feasibility of the "smart primer" concept, a range of materials that are stimulated by UV radiation with different theoretical densities, particle size, and emission intensities were selected to identify properties that most influence primer luminescence.

1. UV Stimulation to IR Emission

FIG. 1 is a schematic for a smart coating for damage and flaw detection according to an exemplary aspect of the present invention. By way of example, FIG. 1 illustrates a structural component, such as a ferrous-based structural component, having a UV reactive region with an outward surface. Examples of an appropriate UV reactive layer materials include, but are not limited to $CaS;Yb^{2+}$; $CaS:Yb^{2+}$, $Cl^-$; $CdS:Ag^+$, $Cl^-$; $CaTiAlO_3:Bi^+$; $NaKErTiSi)11:Eu^{3+}$, $ZnS:RE$, $MgWO_4:RE$, $CaWO_4:RE$, and sulfides, oxides or fluorides doped with RE (where RE is one or more of the rare earth elements). The structural component may be any ferrous or non-ferrous material. The structural component may be an alloy material: ferrous alloys such as, A36 hot rolled, 1018, cold rolled, HY80, high alloy steel structures; non-ferrous alloys such as, Inconel and similar high temperature alloys, 6061 aluminum alloys and similar, aerospace alloys Ti6A14V and similar; non-metallic materials such as, epoxyglass composites, engineered ceramic tiles as used in ballistic armor, or mixed alloy or composite combinations. The stimulation wavelength ranges from 200 to 450 nanometers (nm) with resulting emission wavelengths from 750 to 3000 nm for one aspect of the invention. It should be appreciated that the outward surface could also be an inner/internal region. The region below the outward surface or the UV reactive region exhibits a different response to UV, visible, or IR illumination providing contrast between flawed areas and non-defected areas. Similarly, multiple regions that provide different electromagnetic response(s) can be used in the present invention, according to the technique shown in FIG. 1, to provide contrast of damage based on damage penetration depth. The damaged or flawed region within the coating/coating system or component does not have to be exposed through the coating surface in order to be detected, since IR can transmit through most coatings. IR luminescent coating layers may also be used in coating systems to show the uniformity or sub-layers for components.

According to an exemplary embodiment of the present invention, multi-layer coatings have been produced with an organic-metallic UV responsive primer coating in an organic aliphatic top coat. Damage that penetrates the aliphatic top coat of the coating emits green visible luminescence when exposed to UV illumination. By way of experimentation, initial component samples, two- and three-layer paint systems are used with the UV reactive concept of the present invention to be incorporated into a Zinc Rich Primer layer.

The incorporation into a coating system of UV stimulated phosphors which emit IR radiation adds additional benefits to those previously mentioned for UV stimulation to visible emission. For example, IR emission from a damage site should transmit farther than most visible wavelength emitting phosphors and should be a very efficient stimulation of low energy IR waves from higher energy UV waves. Other benefits include the fact that IR emitting smart coatings are less prone to false positives for damage sites as opposed to visible wavelength emitting coatings since there is not interference from other visible colors. Within the emission wavelengths, short wavelengths (750-1250 nm) IR is easily detected using commercially available video and photography equipment which should help reduce detection costs. Resulting emissions can provide both quantitative and qualitative data. For example, both color and intensity of the emission spectrum may provide detection information about the wear, corrosion, damage, failure, flaws, and/or defects incurred.

2. UV Stimulation to Visual Emission

FIG. 2 shows UV interactive coating and coating systems for nondestructive evaluation and detection of corrosion, failure, damage, flaw, and/or defects. By way of example, FIG. 2 illustrates a schematic of a three-layer system having an iron-based structural component with a primer having luminescence pigments. The structural component may be non-ferrous. The primer with luminescence pigment has an intermediate coat with a top coat. Examples of luminescence pigments include, but are not limited to ZnO:S, CaO:Eu$^{3+}$, TiO$_2$:N$^+$, CaO: RE (where RE is one or more of the rare earth elements, ZnO:RE, any oxide ZrO$_2$—Y$_2$O$_3$—RE, TiO$_2$—ZrO$_2$—RE, SiO$_2$—Al$_2$O$_3$—RE, or nitride doped with RE (where RE is one or more of the rare earth elements). A preferred pigment includes ZnO:S for primer- type pigments that have high solids loadings. These pigments could be used in primer types, such as Zn-based primers. Example topcoats include polyester based high gloss polyurethane with or without well dispersed oxides. FIG. 2 should not be construed as being limiting to the scope of the present invention. For example, it should be appreciated that the UV reactive coating can be incorporated into any layer or functionally-graded organic/metallic coating system, a coating having greater than two layers, or metallic, ceramic, polymer, or composite substrate. The present invention is not limited to Fe-based systems/substrates to detect corrosion. The present invention contemplates use with other alloys. Further, the present invention should not be construed as being limited to aliphatic top coats. The present invention is applicable to all paint systems that accommodate electromagnetic interactive responsive materials. For example, a UV phosphor material could be incorporated into a primer or coating system. The primer or coating system would provide a new method of nondestructive evaluation of coated structures which would eliminate the need for costly consumables used in traditional NDE techniques, such as MPI and FDP. Furthermore, the primer, surface or coating system of the present invention would make damage more visible from farther viewing distances than traditional visual inspection which makes inspection of larger structures, such as bridges and boats, much easier.

For example, large scale evaluation with IR illumination can be accomplished using IR spot and flood lights which produce an invisible, safe and effective excitation source, even at 100+ meters away from the inspection site. Using up-conversion phosphors, large structures could be inspected for damage at a distance whereby the defected or cracked surface area is easily and rapidly detected.

Additionally, the primer coating system distinguishes a series of subsurface damage from minor subsurface or surface defects, allows faster and more thorough inspection of painted structures than traditional visual inspection, and has a higher efficiency and brighter luminescence. Other additional benefits for UV stimulation to visible emission for coatings and coating systems for damage and flaw detection include coverage evaluation/post-inspection of coating process, damage/flaw detection of luminescent layer subsequent to the coating process or pre-inspection for further coating applications, and increased inspection rates of damage to protective layers for coated components, such as damage of erosion, corrosion, impact, abrasion, blistering, and a failure of protective regions exposing luminescent layers for inspection. The present method would also provide a means to evaluate the extent of damage of components (distinction of damaged regions based on luminescent region/regions exposed), and a method for quantitative evaluation of structural health using digital image analysis.

For example, with the luminescent primers, damaged coatings can be evaluated for extent of damage. Qualitatively, the present invention allows distinguishment of damage that penetrates the top coat, intermediate and primer by not only contrast but color as well. Using commercial digital image analysis software, the damage can be rapidly quantified and selected damaged areas can be measured for size, shape, or total percentage of part area. One example of quantitative evaluation includes viewing a damaged site by UV illumination, deciphering damage to the Zinc Rich Primer (ZRP) selected and highlighted in red, distinguishing when damage is in excess of the primer or deeper surfaces by a yellow illumination, identifying bare exposed metal in an auburn color, and distinguishing the exposed Mg-doped In$_x$O$_y$ (MIO) intermediate layer in pink. Based on the color characterization of the damaged areas, these selected areas can be measured for size, shape, or total percentage of part area.

Figure 3:
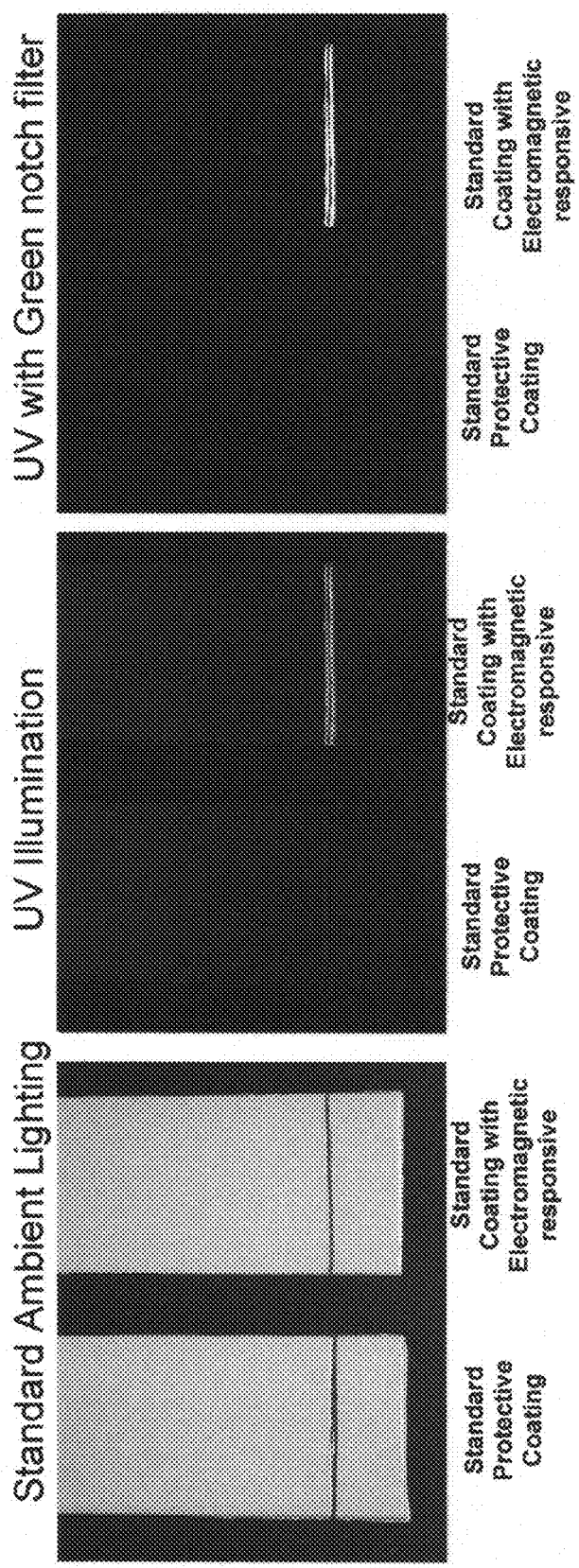
FIG. 3 is a picture illustration of a comparison of a standard 2 layer protective coating used for structural steel with a 2 layer coating of the present invention under different illuminations providing improved damage protection.

FIG. 3 illustrates comparisons of the standard two-layer protective coating used for interiors of structural steel with a "smart" coating of the present invention. The "smart" coating clearly exhibits increased damage detection properties. For example, under UV illumination, the damage is much more apparent from a distance and exhibits increased intensity and color contrast. Furthermore, this contrast can be magnified greatly using notch filter visual inspection. It should be noted that for multi-layer paint systems, damage detection may be determined using a specific luminescent material or material systems incorporated into the formulation of the coating/coating system. Materials used for the "smart" coating illustrated in FIG. 3 include, by way of example, CaO: Eu and ZnO:S.

Figure 4:
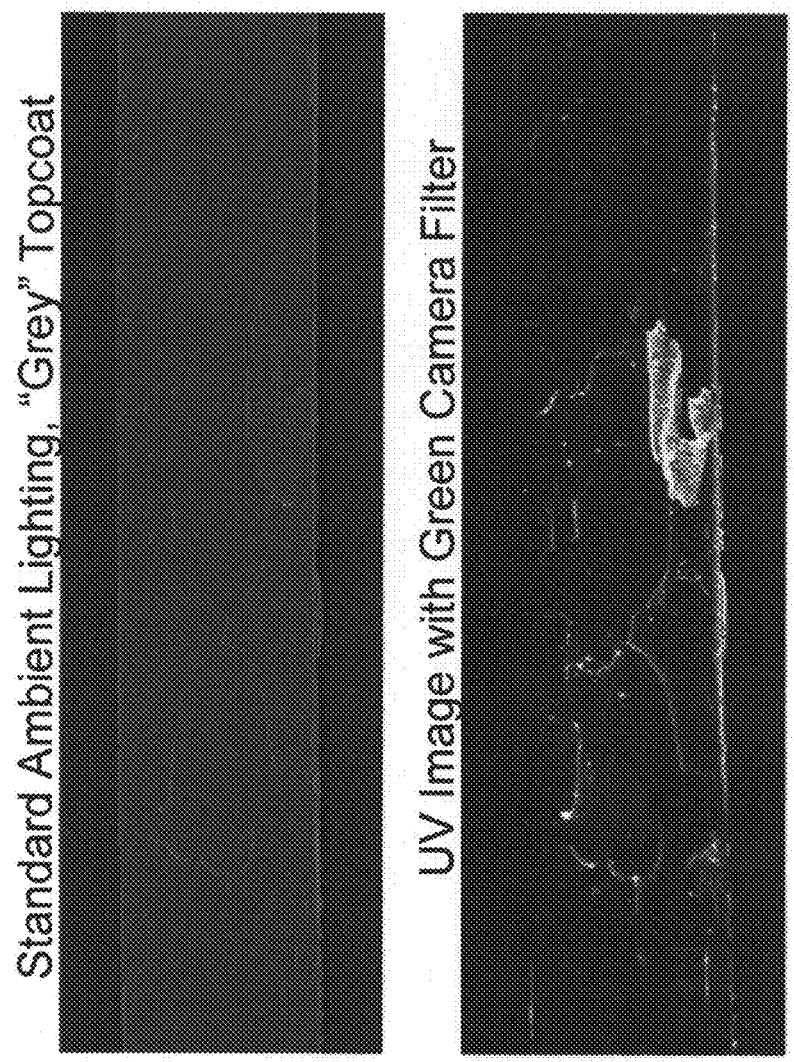
FIG. 4 illustrates the difference in emission of a sample of the present invention using standard ambient lighting versus UV imaging according to an exemplary embodiment of the present invention.

FIG. 4 further illustrates the added benefit of contrast for visual inspection and detection of damage of a protective coating. Because damaged surfaces are often obscured by surface factors, such as glare, surface finish, dirt, corrosion, and imparted paint from objects and impacting surfaces, damage may only be visible with close and meticulous inspection. Notwithstanding, the present invention allows for rapid damage detection of a coating using UV reactive layers such as ZnO:S; ZnO:RE, and in combination with UV inspection.

Figure 5:
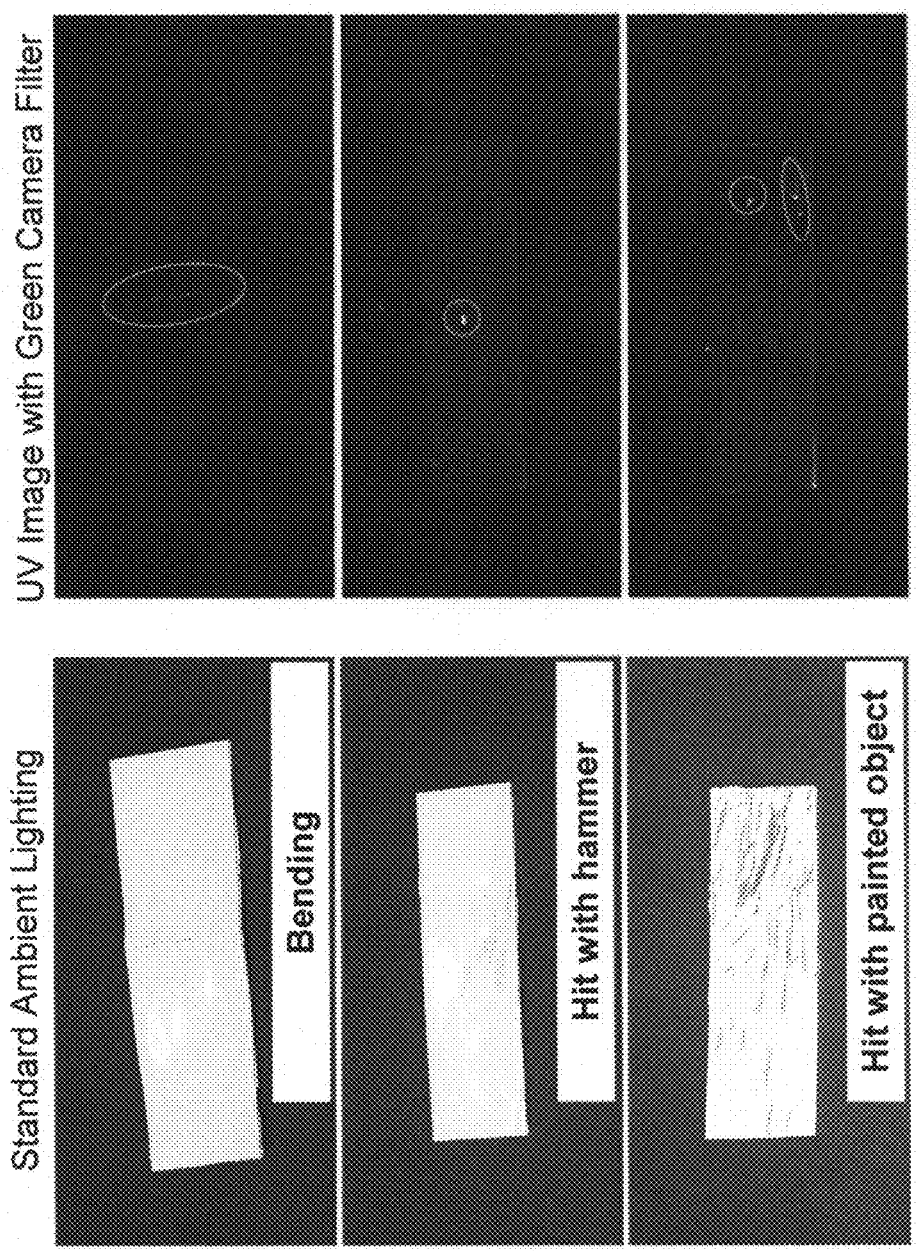
FIG. 5 illustrates photos of various types of damages that could be imparted to painted structures and inspection by both visual light and improved UV inspection with color filters according to one aspect of the present invention.

FIG. 5 illustrates photos of various types of damages that could be observed imparted on painted structures and inspection by both visual light and UV inspection with color filters according to one aspect of the present invention. Shown in the left column of images in FIG. 5 are examples of how visual inspection under ambient light conditions fails to provide the contrast needed to accurately detect damaged areas. Highlighted in circles in the right column of the images in FIG. 5 are damaged regions easily distinguished by the added contrast of the UV reactive layer and UV inspection. By way of example, the bright green areas shown in the right column indicate damage depth to the Zinc Rich Primer.

3. IR Up-Conversion to IR Emission

FIG. 6 shows a schematic for TR up-conversion to IR emission surface, coating and coating systems for subsurface damage, blistering and flaw detection. The schematic illustrates how a damaged primer layer can be detected as a dark region (or bright region depending on contrast) using IR detecting photography or video equipment. For example, FIG. 6 illustrates an iron-based structural component having a primer with IR luminescence and subsequent coats including an intermediate coat and a top coat. In essence, the iron-based structural component shows as a dark region using IR detecting photography or video equipment. The present invention should not be construed as being limited to Fe-based systems/substrates to detect corrosion. The present invention contemplates use with unlimited other alloys. The example of IR up-conversion to IR emission shown in FIG. 6 uses stimulation wavelengths (750-3000 nm) and emission wavelengths (750-3000 nm). As many coatings and paints are more transparent to IR light than UV light, additional benefits are derived from stimulating with IR light. For example, IR light can be used to inspect the entire subsurface of a coated object rather than only the damaged areas. As such, the present invention may be used to inspect the integrity of subsurface regions and layers in areas such as erosion/corrosion inspection, adhesion inspection, presence of the layers needed for multi-region systems, and the like. This may include, by way of example, evaluation of a primer layer of a multi-layer system to determine subsurface corrosion before formation of a blister or evaluation of the coating system to determine the consistent presence of a luminescent region or layer that inhibits transmission of EM waves or radiation. Other examples of application include nondestructive evaluation of pipes/storage containers for degradation. A storage container is known to be translucent/transparent to IR wavelengths of inspection and emission. Thus, the storage container may have an internal luminescent coating to meter degradation inside of the closed container. Examples of materials suitable for use in the primer as a luminescent include YAG:RE, YAP:RE, YAM:RE, YAlO$_3$:RE, and SiO2, Al2O3, TiO2, HfO2 individual or mixed combinations with dopants that include RE.

4. IR Down-Conversion to IR Emission

FIG. 7 discloses yet another exemplary aspect of the present invention. In particular, FIG. 7 illustrates IR down-conversion to IR emission for surface, coating and coating systems for subsurface damage and flaw detection. Like IR up-conversion to IR emission for coatings and coating systems for subsurface damage and flaw detection shown in FIG. 6, IR down-conversion to IR emission may be used for the same applications. Using down-conversion stimulation to IR emission provides greater emission efficiency. For example, down-conversion stimulation provides better EM wave interactions for stimulation and emission in various applications, such as subsurface analysis of large engineering structures (bridges, buildings, military components, cars, and the like). Down-conversion stimulation also provides better accuracy and efficiency in corrosion and general coating defect detection, monumental cost savings and increased product lifetimes of coated structures or components. IR emission offers several advantages. IR waves can be used to determine the thickness of the coatings to be used in both IR up- and down-conversion to IR emission, as shown in FIGS. 6 and 7. Furthermore, by altering the thickness of the coatings, the coatings can absorb IR energy and produce different emission to reduce or enhance detection. Examples of materials suitable for use in the system illustrated in FIG. 7 include $ZrO_2$—$Y_2O_3$—RE oxide, $Al_2O_3$—$Y_2O_3$—RE oxide, $Al_2O_3$—$SiO2$—RE oxide, or fluorides. A preferred material of the present invention includes $Al_2O_3$—$Y_2O_3$—RE oxide.

5. IR Up-Conversion to Visible Emission

FIG. 8 illustrates another aspect of the present invention. FIG. 8 is a schematic illustrating how damage to the depth of a primer can be detected using IR stimulated up-conversion pigments which are visibly luminescent. IR up-conversion to visible luminescence offers significant advantage over UV stimulation to visible luminescence. For example, IR is a safer stimulation source that is less harmful to people and requires minimal safety precautions to operate. IR stimulation sources can also be transmitted farther distances in air and use less electricity than comparable UV sources making them ideal for evaluating large structures, such as bridges. IR stimulation sources can penetrate deeper into a wider variety of top coat materials, such as polyeurathanes, polysilanes, or polycarbonates, and/or mixes or hybrids, and can stimulate visual emission from cracks or defects through the coating rather than through the defects, as with the UV stimulated phosphors. The example of IR up-conversion to visible emission, shown in FIG. 8 uses for example stimulation wavelengths (750-3000 nm) and emission wavelengths (450-750 nm). Some examples of materials suitable for use as an IR up-conversion primer shown in FIG. 8 comprise $Al_2O_3$—$Y_2O_3$—RE oxide.

6. Any combination of 1-5, above.

The present invention could use multiple materials, layers, coatings and/or coating systems having multiple excitation/emission frequencies.

It should be understood and appreciated from the aforementioned description of the present invention that the various aspects of the present invention are not to be inferred as mutually exclusive. For example, a coating may be produced that produces a visual response under UV illumination to determine coverage that will also produce an IR response for thickness measurements or subsurface degradation. Similarly, the present invention is not to be construed to be limited to one single material, as a luminescent material may have multiple stimulation and emission frequencies and nearly infinite material combinations and wavelengths of interaction. Rather, the present invention focuses on broad electromagnetic stimulation and emission ranges, whether wavelength, photon energy, wave number, or the like. The present invention also contemplates multiple wave interactions for stimulation and emission, such as multi-component material(s) that have multi-excitation frequencies or emission frequencies. Some examples include an up-conversion phosphor, multiple luminescent pigments in a coating that interacts with different wavelengths of stimulation, luminescent pigment in a coating that emits a wavelength that stimulates a second pigment. Furthermore, the present invention contemplates that the electromagnetic responsive coatings are clearly defined by each individual layer where coating operations are used to produce the final product whether graded, composite, monolithic coatings, multilayer, or mixed combination, or the like. Notwithstanding, the various coating layers, it should be appreciated that the electromagnetic response can be generated by, but should not be limited to pigments, additives, polymer modifications, intrinsic monolithic materials, or the like. The present invention also further contemplates additional variations or incorporations with an intermediate layer or multilayer coating system, as well as mixed detection modes or formulations that provide different luminescent signatures depending on the coating or coating system design that would also allow tailoring for a particular failure generation mechanism. Additional features to allow tailorability of the surface, coating, or coating system could include surfactants, dispersants, particle size, particle size distribution, morphology, composition, and the like.

The embodiments of the present invention has been set forth in the drawings and specification and although specific terms are employed, these are used in the generically descriptive sense only and are not used for the purposes of limitation. Changes in the formed proportion of parts as well as in the substitution of equivalence are contemplated as circumstances may suggest or are rendered expedient without departing from the spirit and scope of the invention as further defined in the following claims.

Any references in the Specification are herein incorporated by reference in their entirety.

What is claimed is:

1. A coating for non-destructive detection and evaluation of surfaces and sub-surfaces comprising: a host material adapted for coating and adhering to a surface of a structure or member, a luminescent material incorporated into and compatible with the host material; the luminescent material having an emission response when stimulated by stimulation means to indicate areas of concern in the host material; the emission response at a flaw in the host material being less detectable than the emission response from the host material and having a contrast from the host material.

2. The coating of claim 1 wherein the stimulation means comprises at least one of:
   a. an electromagnetic stimulate; or
   b. a thermal stimulate.

3. The coating of claim 1 wherein the host material comprises at least one of:
   a. a primer coating;
   b. an intermediate coating; or
   c. a top coating.

4. The coating of claim 1 wherein the luminescent material comprises a UV phosphor.

5. The coating of claim 4 wherein the stimulation means comprises a UV stimulate.

6. The coating of claim 5 wherein the UV stimulate ranges in wavelength from 1 nm to 450 nm.

7. The coating of claim 5 wherein the emission response comprises visible emission ranging in wavelength from 450 nm to 750 nm.

8. The coating of claim 1 wherein the host material comprises a visibly luminescent layer.

9. The coating of claim 1 wherein the emission comprises IR emission ranging in wavelength from 750 nm to 3000 nm.

10. The coating of claim 1 wherein the host material comprises an IR up-conversion layer or an IR down-conversion layer.

11. The coating of claim 10 wherein the stimulation means comprises an IR stimulate ranging in wavelength from 750 nm to 3000 nm.

12. The coating of claim 10 wherein the emission comprises IR emission ranging in wavelength from 750 nm to 3000 nm.

13. The coating of claim 10 wherein the stimulation means comprises an IR stimulate ranging in wavelength from 750 nm to 3000 nm.

14. The coating of claim 10 wherein the IR up-conversion comprises a visible emission response ranging in wavelength from 450 nm to 750 nm.

15. A system providing non-destructive detection and evaluation of surfaces and sub-surfaces of a member or structure, the system comprising:
   a host member comprising a surface, wherein integrity detection and evaluation of the surface is desired;
   one or more coatings covering the surface of the host member;
   a luminescent material incorporated into and compatible with the one or more coatings;
   interrogation means comprising a stimulate;
   the luminescent material stimulated by the stimulate emitted from the interrogation means and providing an emission response to indicate flaws in the one or more coatings on the host member;
   a flaw in the one or more coatings, the flaw having a response less detectable than the emission response surrounding the flaw.

16. The system of claim 15 wherein the coating comprises at least one of:
   a. an IR energy responsive coating;
   b. a visible energy responsive coating;
   c. a UV up-conversion responsive coating; or
   d. a UV down-conversion responsive coating.

17. The system of claim 15 wherein the luminescent material comprises a phosphor having:
   a. a luminescent center of the coating; or
   b. a second phase of the coating.

18. The system of claim 17 wherein the second phase comprises a pigment.

19. The system of claim 17 wherein the second phase comprises a molecular side or end group attached to a primary or secondary component of the coating.

20. The system of claim 15 wherein the one or more coatings comprise:
   a. a primer layer;
   b. an intermediate layer; and
   c. a topcoat layer.

21. The system of claim 20 wherein the luminescent material is incorporated into at least one of the primer, intermediate or topcoat layer.

22. A method for non-destructively detecting and evaluating surface and subsurface regions of a member or structure, the method comprising:
   providing a member or structure wherein integrity detection and evaluation of surfaces and sub-surfaces of the member or structure are desired;
   incorporating a UV phosphor material into a coating compatible with the luminescent material and surface of the member or structure;
   applying the coating to the surface of the member or structure;

stimulating the luminescent material in the coating with an electromagnetic stimulate; and detecting an emission response from the luminescent material to identify a flaw in the coating, the flaw having a weaker response to the electromagnetic stimulate than the coating proximate the flaw.

23. The method of claim 22 further comprising the step of stimulating the luminescent material with a UV stimulate ranging in wavelength from 200 nm to 450 nm and evaluating an IR emission response ranging in wavelength from 750 nm to 3000 nm.

24. The method of claim 22 wherein the coating comprises an IR up-conversion coating or an IR down-conversion coating.

25. The method of claim 24 further comprising the step of stimulating the luminescent material with an IR stimulate ranging in wavelength from 750 nm to 3000 nm and evaluating an IR emission response having ranges in wavelength from 750 nm to 3000 nm.

26. A coating system for detecting flaws in coated surfaces, the system comprising:
- a surface having a flaw, the flaw having a response;
- a coating covering the surface;
- a luminescent material in the surface coating, the surface coating having an emission response; and
- a detection of the flaw in the surface comprising the emission response from the coating being greater than the response from the flaw in the surface.

* * * * *